(12) United States Patent
Kim

(10) Patent No.: US 8,364,425 B2
(45) Date of Patent: Jan. 29, 2013

(54) METHOD AND SYSTEM FOR DETERMINING PROPERTIES OF AN ASPHALT MATERIAL

(75) Inventor: Sang-Soo Kim, Athens, OH (US)

(73) Assignee: Ohio University, Athens, OH (US)

( * ) Notice: Subject to any disclaimer, the term of this patent is extended or adjusted under 35 U.S.C. 154(b) by 0 days.

(21) Appl. No.: 13/226,137

(22) Filed: Sep. 6, 2011

(65) Prior Publication Data

US 2012/0016601 A1 Jan. 19, 2012

Related U.S. Application Data

(63) Continuation-in-part of application No. 11/994,569, filed as application No. PCT/US2006/026193 on Jul. 5, 2006, now abandoned.

(60) Provisional application No. 60/696,643, filed on Jul. 5, 2005.

(51) Int. Cl.
*G01L 1/00* (2006.01)
(52) U.S. Cl. .................................................. 702/41
(58) Field of Classification Search .............. 702/41–43
See application file for complete search history.

(56) References Cited

U.S. PATENT DOCUMENTS

| | | | |
|---|---|---|---|
| 4,841,226 | A | 6/1989 | Meline et al. |
| 5,187,987 | A | 2/1993 | Anderson |
| 5,248,200 | A | 9/1993 | Walsh |
| 5,363,701 | A | 11/1994 | Lee et al. |
| 5,487,307 | A | 1/1996 | Landgren et al. |
| 2002/0032531 | A1 | 3/2002 | Mansky et al. |
| 2002/0167988 | A1 | 11/2002 | Zhu |

FOREIGN PATENT DOCUMENTS

SU 587376 1/1978

OTHER PUBLICATIONS

The International Search Report for PCT/US2006/026193, mailed Oct. 27, 2006.
The Written Opinion of the International Searching Authority for PCT/US2006/026193, mailed Oct. 27, 2006.
C.-S. Oh, W.N. Sharpe, Jr., Techniques for measuring thermal expansion and creep of polysilicon, Sensors and Actuators, vol. 112, No. 1, pp. 66-73, XP004504727, Apr. 15, 2004, Elsevier Sequoia S.A., Lausanne, CH.
Surendra P. Shah, Chengsheng Ouyang, Shashidhara Marikunte, Wei Yang, Emilie Becq-Giraudon, A Method to Predict Shrinkage Cracking of Concrete, ACI Materials Journal, Title No. 95-M31, pp. 339-346, vol. 95, No. 4, Jul./Aug. 1998.
Dr. James M. Matthews, P.E., Creep Tests for the Rutting Design of Field Highways, Advances in Instrumentation and Control, Instrument Society of America, vol. 50, Part 3, Oct. 1, 1995, pp. 837-847, XP000540056, Research Triangle Park, NC, US.
Y. Richard Kim and Yung-Chien Lee, Interrelationships Among Stiffnesses of Asphalt-Aggregate Mixtures, Asphalt Paving Technology, Association of Asphalt Paving Technologists, vol. 64, Mar. 27, 1995, pp. 575-609, XP008030587, Minneapolis, MN, US.

*Primary Examiner* — Stephen Cherry
(74) *Attorney, Agent, or Firm* — Calfee, Halter & Griswold LLP

(57) ABSTRACT

A method for determining properties of an asphalt material include measuring respective current deformations of a plurality of samples of the asphalt material, repeating the measuring step over a plurality of temperatures that change at a predetermined rate, calculating a plurality of measured total strain values as a function of the deformations and the temperatures, calculating respective creep strains, at different ones of the plurality of temperatures, based on the total strains as a function of applied stresses, calculating respective creep stiffnesses as a function of the temperatures, determining a combined creep curve based on the respective creep stiffnesses, deriving a theoretical creep curve, and fitting the theoretical creep curve with the combined creep curve to determine a master creep curve function and a time-temperature shift function.

15 Claims, 4 Drawing Sheets

METHOD AND SYSTEM FOR DETERMINING PROPERTIES OF AN ASPHALT MATERIAL

This application is a continuation-in-part of U.S. application Ser. No. 11/994,569, filed Jun. 3, 2008, which is a US national phase entry of PCT/US2006/026193 with an international filing date of Jul. 5, 2006, which claims the benefit of U.S. Provisional Application No. 60/696,643, filed Jul. 5, 2005, the entire disclosures of which are hereby incorporated by reference.

BACKGROUND

The present invention relates to determining properties of asphalt. It finds particular application in conjunction with determining a coefficient of thermal expansion, a master creep modulus, and a temperature shift function and will be described with particular reference thereto. It will be appreciated, however, that the invention is also amenable to other applications.

The task of determining viscoelastic properties of materials (including asphalt binder and polymers) is routinely performed for product development and product performance evaluation. To have complete rheological spectrum over a wide range of temperatures and loading rates, many tests at different temperatures and loading rates are performed. Therefore, the number of required tests, the task of determining viscoelastic properties of materials is labor intensive and expensive. As a result, many tests for quality control/quality assurance (QC/QA) are not completed. In some cases, such lack of QC/QA testing results in unsatisfactory performance of viscoelastic materials.

Coefficient of thermal expansion (CTE) is a parameter used for determining thermal stress development within asphalt pavement. However, there is currently no easy to use reliable method for testing CTE. Even though a dilatometric method has been used to study CTE of asphalt binders, its complex test procedure prohibited a routine use of this method.

The present invention provides a new and improved method and apparatus which addresses the above-referenced problems.

SUMMARY

In one aspect of the present invention, it is contemplated to determine properties of an asphalt material by measuring respective current deformations of a plurality of samples of the asphalt material, repeating the measuring step over a plurality of temperatures that change at a predetermined rate, calculating a plurality of measured total strain values as a function of the deformations and the temperatures, calculating respective creep strains, at different ones of the plurality of temperatures, based on the total strains as a function of applied stresses, calculating respective creep stiffnesses as a function of the temperatures, determining a combined creep curve based on the respective creep stiffnesses, deriving a theoretical creep curve, and fitting the theoretical creep curve with the combined creep curve to determine a master creep curve function and a time-temperature shift function.

BRIEF DESCRIPTION OF THE DRAWINGS

In the accompanying drawings which are incorporated in and constitute a part of the specification, embodiments of the invention are illustrated, which, together with a general description of the invention given above, and the detailed description given below, serve to exemplify the embodiments of this invention.

DETAILED DESCRIPTION OF ILLUSTRATED EMBODIMENT

Analysis of low temperature thermal cracking behavior of an asphalt binder requires rheological and thermal properties as inputs. Just as all other viscoelastic materials, the response of an asphalt binder to an applied load is loading rate and temperature dependent. A master modulus curve and shift factor function characterize these rate and time dependencies, respectively. The construction of a reliable master curve and shift factor function is time consuming and labor intensive, which requires repeating many isothermal rheological tests (such as creep test, uniaxial compression test, or direct tension test) at several temperatures. A prediction for the thermal stress development in an asphalt and an asphalt mixture require accurate coefficients of thermal expansion/contraction (CTE) values.

The test device, test procedure, and/or analysis software presented herein are used to determine three (3) properties of an asphalt binder from a single temperature swipe (from about −60° C. to about 25° C.) of five (5) asphalt binder specimens. More specifically, the three (3) properties determined by the test device, test procedure, and/or analysis software include: 1) master creep stiffness curve; 2) shift factor function; and 3) CTE.

Figure 1:
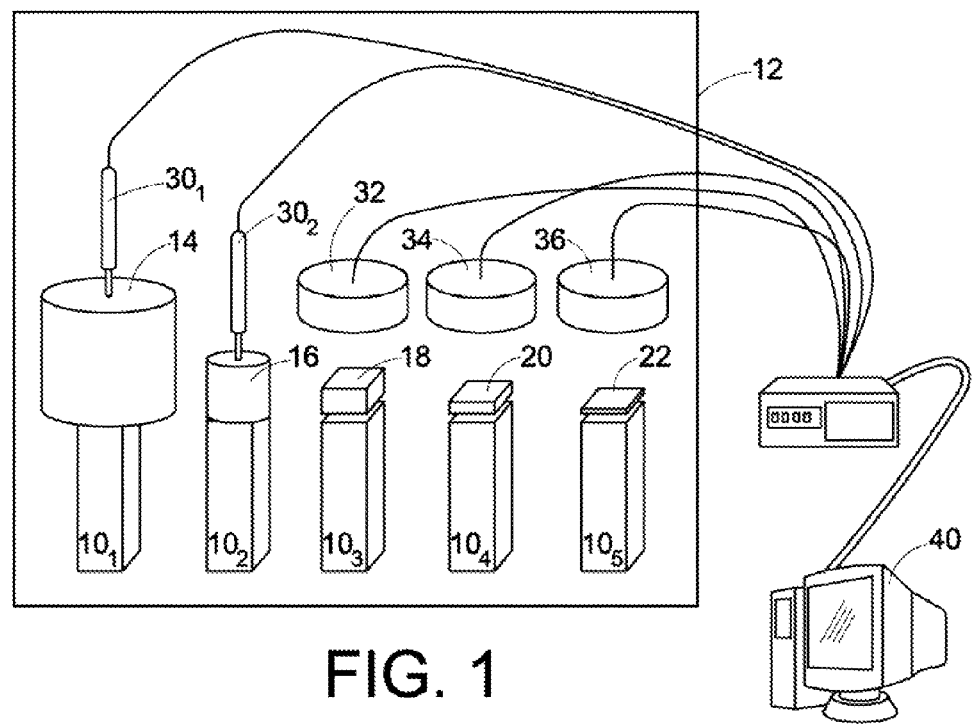
FIG. 1 illustrates a schematic representation of a system in accordance with one embodiment of an apparatus illustrating principles of the present invention.
Figure 2:
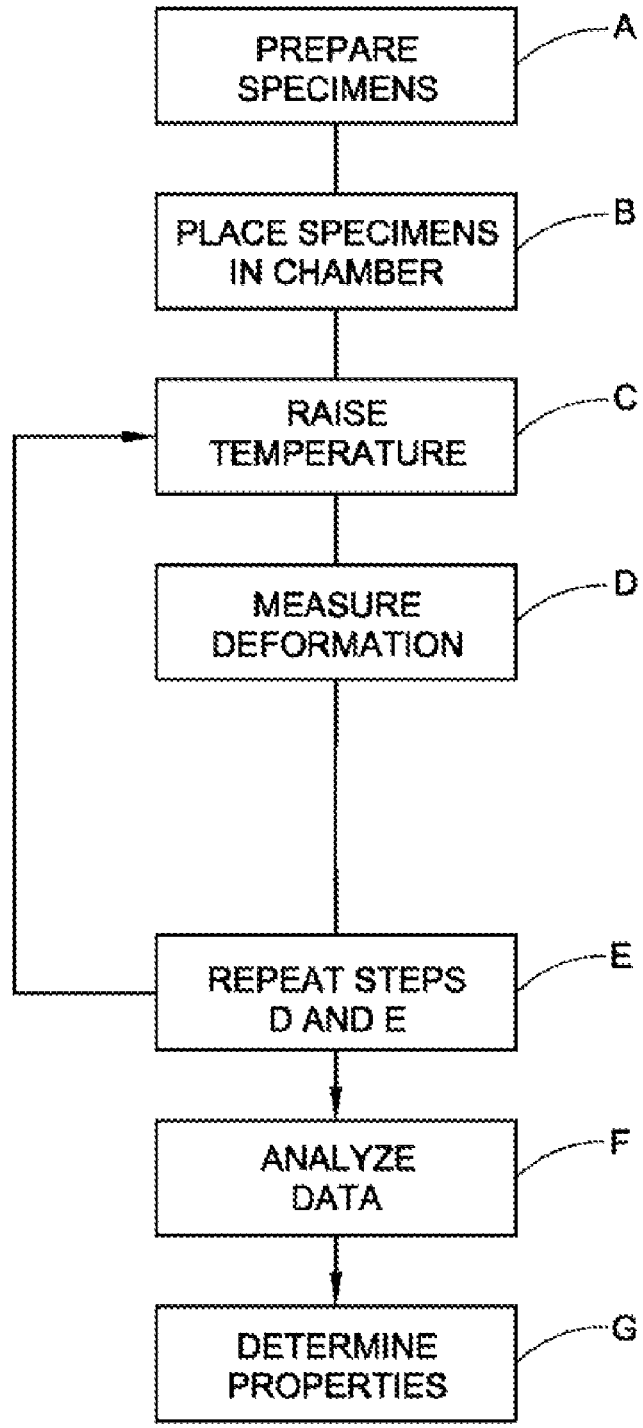
FIG. 2 illustrates an exemplary methodology in accordance with one embodiment illustrating principles of the present invention.

With reference to FIGS. 1 and 2, specimens of asphalt material are prepared in a step A. In the illustrated embodiment, five (5) specimens $10_1$, $10_2$, $10_3$, $10_4$, $10_5$ are prepared. In one embodiment, each of the specimens $10_1$, $10_2$, $10_3$, $10_4$, $10_5$ is molded to have dimensions of about 25.4 mm (height)× about 12.7 mm (width)×12.7 mm (depth). In a step B, each of the specimens $10_1$, $10_2$, $10_3$, $10_4$, $10_5$ is placed inside an environmental chamber 12 having a temperature of about −60° C.

In a step C, a mass 14 of about 10.0 kg is placed on top of the first specimen $10_1$. A mass 16 of about 1.0 kg is placed on top of the second specimen $10_2$. A mass 18 of about 0.1 kg is placed on top of the third specimen $10_3$. In one embodiment, the masses 14, 16, 18 are stainless steel. Plates 20, 22 are molded together with the specimens $10_4$, $10_5$. In one embodiment, the plates 20, 22 are copper and have the same cross-sectional dimensions (e.g., 12.7 mm×12.7 mm) as the specimens $10_4$, $10_5$.

Dimensional changes of the specimens $10_1$, $10_2$ due to temperature changes are measured using, for example, linear variable displacement transducers (LVDT) $30_1$, $30_2$. Dimensional changes of the specimens $10_3$, $10_4$, $10_5$ due to temperature changes are measured using, for example, using non-contact capacitive sensors 32, 34, 36. Non-contact capacitive sensors are used for measuring the dimensional changes of the specimens $10_3$, $10_4$, $10_5$ instead of LVDT's because the small force created by the contact of LVDT's on the specimens $10_3$, $10_4$, $10_5$ would cause significant effects on the load response at ambient to high temperatures. All of the sensors $30_1$, $30_2$, 32, 34, 36 are calibrated for temperature change.

In a step C, the temperature of the chamber 12 is raised a first increment (e.g., about 10° C.) over a period of time (e.g., one (1) hour). In one embodiment, the temperature of the chamber 12 is raised from about −60° C. to about 25° C. in increments of about 10° C. per hour.

In a step D, the deformation (e.g., dimension) of each of the specimens $10_1$, $10_2$, $10_3$, $10_4$, $10_5$ is measured at each of the temperatures in the step C and recorded on, for example, a computing device 40. It is to be understood that the calibrated deformation of the masses 14, 16, 18 and plates 20, 22 are subtracted from the actual measurements. In one embodiment, software is used to determine the CTE, creep stiffness, and shift factor.

The measurement step D is repeated in a step E every predetermined time period (e.g., every 10 seconds) while the temperature of the chamber 12 is raised by returning to the step C. After enough cycles have been measured and the temperature has been raised to about 25° C., control passes to a step F for analyzing the measured data. In the step F, total measured strain, which is a combination of expansive thermal strain and creep strain, is determined as a function of the deformation (e.g., dimension) at the respective temperatures. The coefficient of thermal expansion, a master creep modulus, and temperature shift function are determined in a step G as a function of the measured data analyzed in the step F. The analyzing and determining steps F and G are described in detail below. In one embodiment, the analyzing and determining steps F and G are performed using the computing device 40.

When the temperature is raised from about −60° C. to about 25° C., deformation of each asphalt binder being tested is governed by two (2) mechanisms (e.g., upward thermal expansion and downward creep). The thermal strain as a function of temperature change is calculated as:

$$\varepsilon_{th} = \Delta T \cdot \alpha (\text{constant } \alpha) \text{ or}$$

$$\varepsilon'_{th}(T) = \int_{-60}^{T} \alpha(T') dT' (\alpha \text{ varies with temperature})$$

Where, $\Delta T$=temperature change
$\alpha$=thermal expansion coefficient of asphalt binder Isothermal creep strain as a function of creep stiffness and time is calculated as:

$$\varepsilon_{Creep}(t) = \sigma/S(t)$$

Where, $\sigma$=constant stress due to applied load and weight of asphalt binder
S(t)=creep stiffness of asphalt binder at time t For the transient temperature condition, the creep strain can be obtained using the time-temperature superposition principle where the effect of time duration at one temperature can be expressed by a different time duration at another temperature for the same effect. This relationship is expressed by the temperature dependent shift factor function $a_T(T)$. When time durations at all other temperatures are transformed into a time scale at a single temperature (reference temperature, $T_o$), it is called reduced time. Then, the creep strain at a reduced time, $\tau$, is given as:

$$\varepsilon_{creep}(\tau) = \sigma/S(\tau)$$

Where, $\sigma$=stress due to applied load and weight of asphalt binder
$S(\tau)$=creep stiffness of asphalt binder at reduced time T
$\tau$=reduced time at temperature T (summation of all reduced time between current T and initial temperature −60° C.)=

$$\int_{-60}^{T} \left( \frac{dt/DT}{a_T(T)} \right) dT$$

(dt/DT)=inverse of heating rate
$a_T(T)$=shift factor as a function of T

Total measured strain values of heating experiment at temperature T is simple addition of these two (2) strains. Therefore, since measured strain is a rate of measured deformations, a plurality of respective measured total strain values are calculated from the respective deformations measured at the different temperatures in the step C as follows:

$$\varepsilon_{Total}(T) = \varepsilon_{th}(T) + \varepsilon_{creep}(T)$$

It should be noted that $\varepsilon_{creep}(T)$ cannot be expressed in terms of reduced time, $\tau$, until the shift function is determined.

At low temperatures with slow loading and small strain, the stress-strain (or load-deformation) relationship is linear; strain (and deformation) is proportional to applied stress (and load). By simple algebra, the total strain value of each sample can be separated into $\varepsilon_{th}(T)$ and $\varepsilon_{creep}(T)$. Then, CTE of asphalt binder is determined as:

$$\alpha(T) = d\varepsilon_{th}(T)/dT$$

Figure 3:
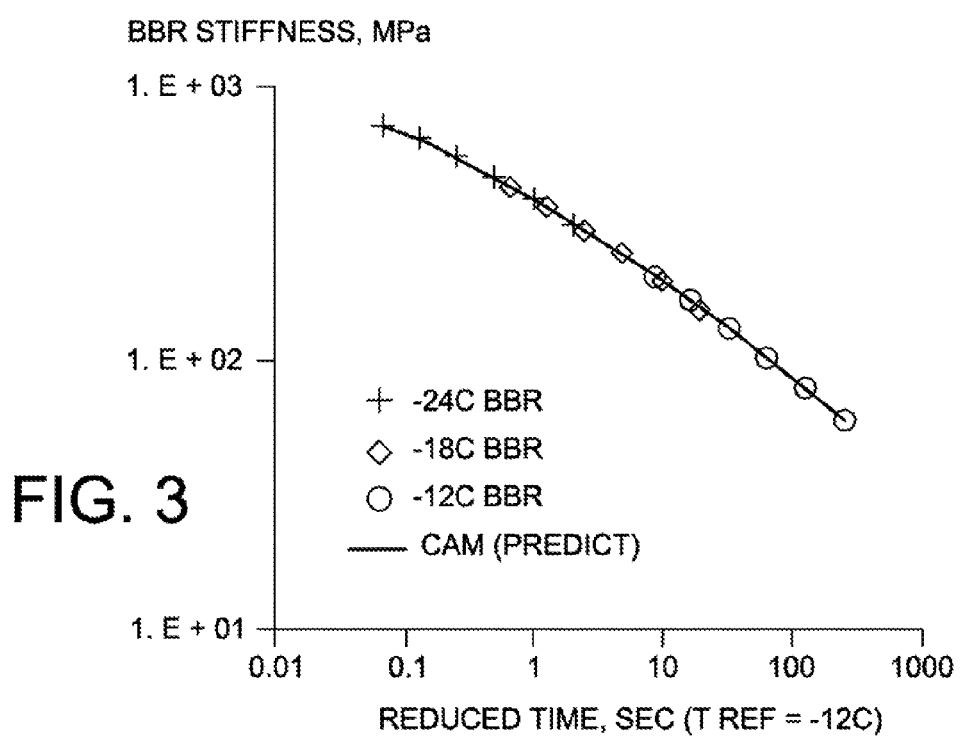
FIG. 3 illustrates an example of a master creep stiffness curve.

A numerical solution for converting $\varepsilon_{creep}(T)$ to $\varepsilon_{creep}(\tau)$ is obtained using master curve and shift factor equations. Master creep curves of asphalt binders have been successfully described by several empirical models. One such model is the Christensen-Anderson-Marasteanu (CAM) model, which describes the master creep stiffness modulus of asphalt in forms of:

$$S(\tau) = S_{glassy}[1 + (\tau/\lambda)^\beta]^{-\kappa/\beta}$$

where, $S(\tau)$=stiffness at reduced time, $\tau$
$S_{glassy}$=glassy modulus of asphalt; constant (3 GPa)
$\tau$=reduced time=$t/a_T(t)$
$a_T(t)$=time-temperature shift factor
$\lambda, \beta, \kappa$=CAM model constants for best fit An example of the master creep curve constructed by manual shifting and comparison with the CAM model are shown in FIG. 3. The CAM model fits the experimental data very well.

The temperature dependency of the shift factors is commonly modeled using the Arrhenius equation for below the glass transition temperatures and WLF equation for above the glass transition temperatures. The Arrhenius equation is more appropriate for the data:

$$\ln(a_T(T)) = a_1(1/T - 1/T_{ref})$$

Where, $a_T$=time temperature shift factor
$a_1$=asphalt dependent constant
T=temperature
$T_{ref}$=reference temperature A numeric solution is found by an optimization program; determining λ, β, κ, and $a_1$ that minimize the differences between measured $\epsilon_{creep}$(T) and predicted $\epsilon_{creep}$(T) by theory.

EXAMPLE

Simulated data is used for this example. The total deformation of five (5) specimens for a −60° C. to 10° C. swipe were calculated based on the linear viscoelasticity theory using an experimentally determined master creep curve and a shift factor function of an asphalt binder (FH WA B6227). A temperature dependent CTE, α(T), for a binder with the similar low temperature characteristics was found in the literature and was used for this example. The total stress on each of the specimens is given in Table 1 and parameters for rheological and thermal properties are given in Table 2.

TABLE 1

Stress acting on the specimens

| Mass | Specimen #1 10 kg | Specimen #2 1 kg | Specimen #3 100 g | Specimen #4 10 g | Specimen #5 1 g |
|---|---|---|---|---|---|
| for metal weight, Pa | 607601.0 | 60760.1 | 6076.0 | 607.6 | 60.8 |
| for sample weight, Pa | 124.5 | 124.5 | 124.5 | 124.5 | 124.5 |
| Total Stress, Pa | 607725.5 | 60884.6 | 6200.5 | 732.1 | 185.2 |

TABLE 2

True parameters

| CAM Model | | | | $a_T$(T) | | α(T) | |
|---|---|---|---|---|---|---|---|
| λ | β | κ | a1 | Tg, (1/° C.) | R | $α_g$, (1/° C.) | $α_1$, (1/° C.) |
| 14.5 | 0.158 | 0.668 | 28684 | −28.2 | 6.21 | 1.16E−04 | 1.96E−04 |

Figure 4:
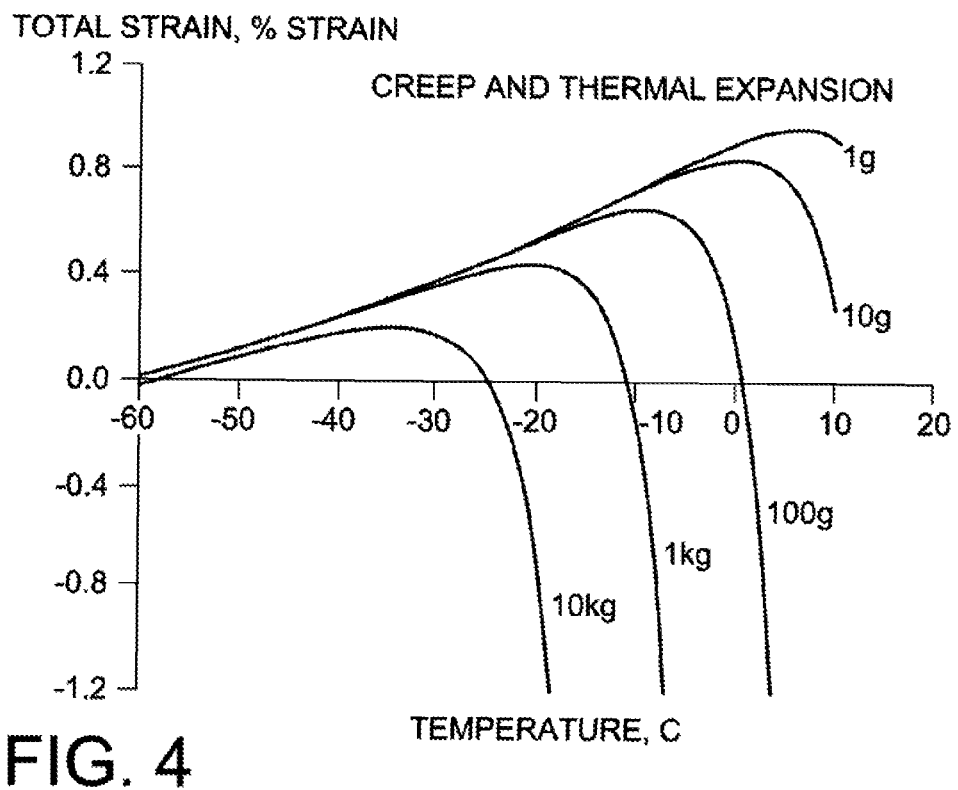
FIG. 4 illustrates simulated responses in accordance with one embodiment of the present invention.

When the test performed on the data, the strain curves illustrated in FIG. 4 are expected to be developed. The viscoelastic theory used for this prediction is known to be very accurate for current testing conditions until a very high strain at elevated temperatures is reached.

The difference between 10 kg total strain and 1 kg total strain (creep strain for 9 kg mass) is:

$$\varepsilon_{total}(T)_{10kg} - \varepsilon_{total}(T)_{1kg} = [\varepsilon_{th}(T)_{10kg} + \varepsilon_{creep}(T)_{10kg}] - [$$

$$\varepsilon_{th}(T)_{1kg} + \varepsilon_{creep}(T)_{1kg}] = \left[\int_{-60}^{T} \alpha(T')dT' + \sigma_{10kg}/S(T)\right] - [$$

$$\int_{-60}^{T} \alpha(T')dT' + \sigma_{1kg}/S(T)\right]\sigma_{10kg}/S(T) - \sigma_{1kg}/S(T) =$$

$$\sigma_{9kg}/S(T) \text{ (creep strain for 9 kg mass)}$$

Strain is the rate of deformation, also known as the rate at which a dimension (e.g., a deformation) changes, divided by the original length. The above equation provides an example for determining respective creep strains, as a function of temperature, for a 9 kg mass (stress) (which is calculated from a difference between total strains for a 10 kg applied mass (stress) and a 1 kg applied mass (stress)). Because all of the specimens have substantially identical cross-sectional areas, the stress is proportional to applied mass. In the above equation, $\epsilon_{total}$(T) represents the total measured strain as a function of temperature, $\epsilon_{th}$(T) represents thermal strain as a function of temperature, and $\epsilon_{creep}$(T) represents creep strain as a function of temperature. Because the creep strain is proportional to the applied mass (stress), but the expansive thermal strain is not dependent upon the applied mass (stress), subtraction of the total strain for 1 kg from the total strain for 10 kg eliminates the expansive thermal strain. Therefore, this equation permits respective creep strains to be calculated at different temperatures as a function of applied stresses.

The above equation may be rearranged for determining respective creep stiffnesses S(T) as a function of temperature:

$$S(T) = \sigma_{9\,kg}/[\epsilon_{total}(T)_{10\,kg} - \epsilon_{total}(T)_{1\,kg}]$$

Figure 5:
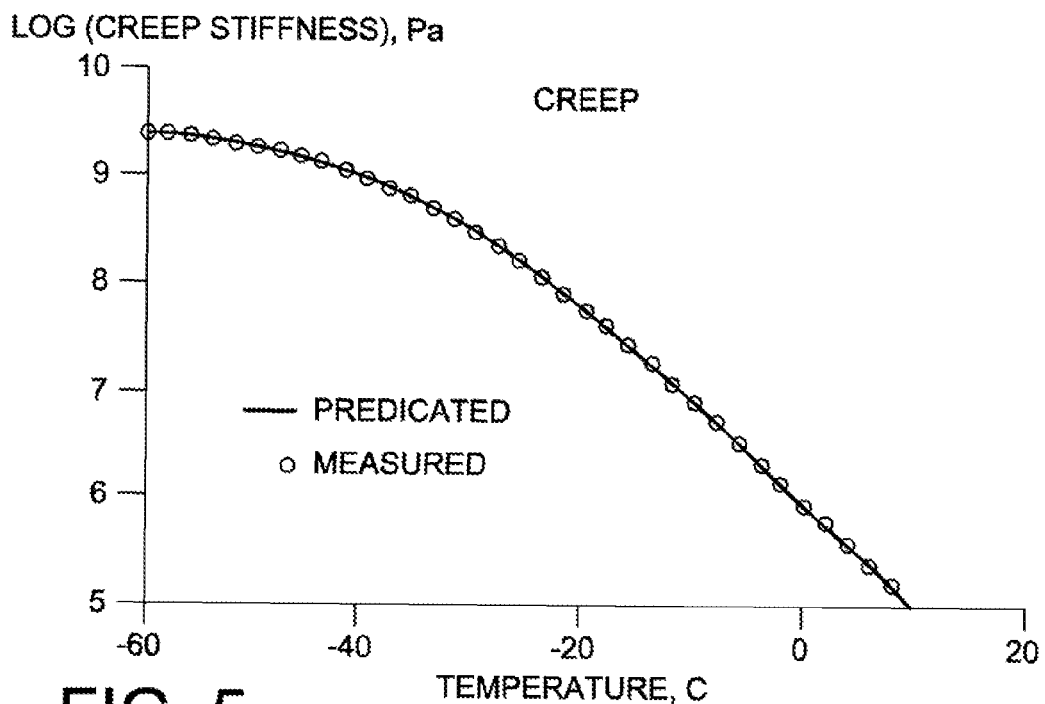
FIG. 5 illustrates predicted versus measured creep curves.

This equation provides a good estimate for a temperature range between about −60° C. to about −25° C. The process is repeated to obtain creep stiffnesses S(T) for other temperature regions (for example, strains from specimens #2 (subjected to 1 kg mass) and #3 (subjected to 100g mass) for about −25° C. to about −5° C. range, and so on). The measured creep stiffnesses at different temperatures are used to generate a combined creep curve, which is illustrated in FIG. 5. In FIG. 5, the circles represent 'measured' values over the entire temperature range.

A theoretical creep curve is derived from a CAM model (a master creep curve function) and Arrhenius equations (a time-temperature shift function). An optimization software is used to fit the theoretical creep curve with the combined creep curve as a function of test time and temperature. The optimization software determines a set of CAM parameters and $a_1$ (which is an Arrhenius equation constant) fitting the measured data best by minimizing a sum of squared errors (SSE). SSE is a sum of squared differences between the measured and predicted creep stiffness for a temperature range. In one embodiment, the CAM parameters and $a_1$ are determined simultaneously. The results of the optimization process converge as shown in Table 3.

TABLE 3

Converging process.

| Iteration | λ | β | κ | a1 | SSE |
|---|---|---|---|---|---|
| 1 | 20.1 | 0.170 | 0.706 | 26760 | 0.000667 |
| 2 | 18.6 | 0.168 | 0.700 | 27146 | 0.000177 |
| 3 | 19.3 | 0.170 | 0.705 | 26789 | 0.000439 |
| 4 | 15.4 | 0.166 | 0.685 | 27630 | 0.000360 |
| 5 | 18.3 | 0.166 | 0.694 | 27358 | 0.000362 |
| 6 | 18.4 | 0.166 | 0.695 | 27399 | 0.000123 |
| 7 | 18.4 | 0.167 | 0.696 | 27330 | 8.75E−05 |
| 8 | 18.5 | 0.168 | 0.698 | 27190 | 0.000119 |
| 9 | 18.3 | 0.167 | 0.697 | 27290 | 0.000104 |
| 10 | 18.4 | 0.167 | 0.697 | 27265 | 9.18E−05 |
| 11 | 18.5 | 0.167 | 0.697 | 27274 | 7.92E−05 |
| 12 | 18.4 | 0.167 | 0.697 | 27275 | 8.14E−05 |
| 13 | 18.5 | 0.167 | 0.697 | 27276 | 7.71E−05 |
| 14 | 18.5 | 0.167 | 0.697 | 27276 | 7.74E−05 |
| 15 | 18.5 | 0.167 | 0.697 | 27275 | 7.71E−05 |
| 16 | 18.5 | 0.167 | 0.697 | 27276 | 7.71E−05 |
| 17 | 18.5 | 0.167 | 0.697 | 27275 | 7.70E−05 |
| 18 | 18.5 | 0.167 | 0.697 | 27275 | 7.70E−05 |

Figure 6:
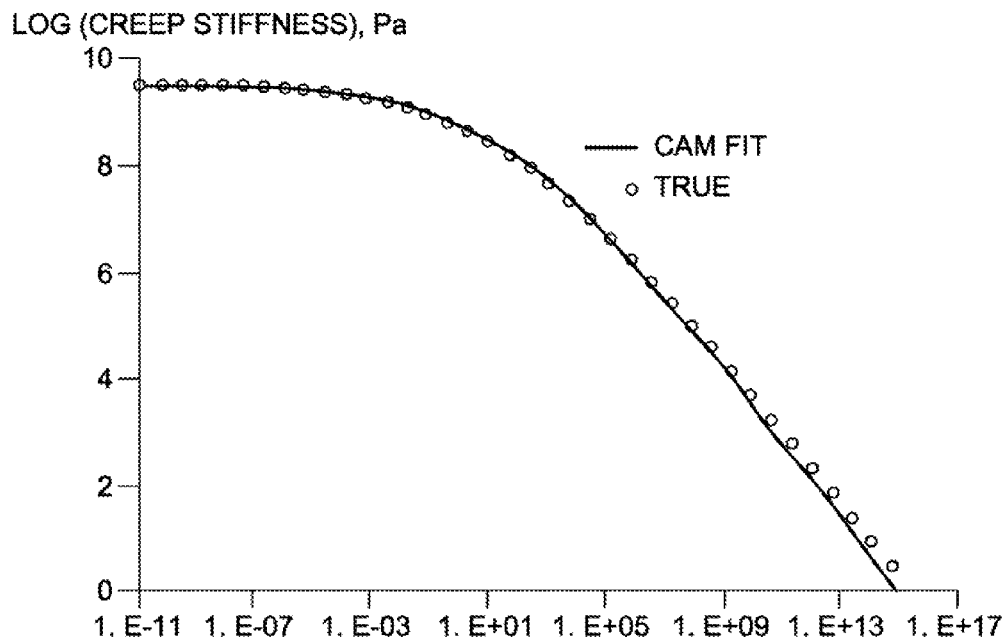
FIG. 6 illustrates a master creep curve as a function of reduced time.

Each iteration performs calculations for 1000 combinations of four (4) parameters and chooses the best set. After 13 iterations the SSE (sum of square error) of log stiffness converged to a minimum. The creep curve predicted by this optimization software is also plotted in FIG. 5 (solid line). The CAM parameters and shift factor constant determined by this process are given in Table 4. The master creep curve as a function of reduced time is illustrated in FIG. 6.

TABLE 4

CAM parameters and shift factor constant; true vs. predicted

| | CAM Model | | | $a_T(T)$ | $\alpha(T)$ | | | |
|---|---|---|---|---|---|---|---|---|
| Parameter | λ | β | κ | a1 | Tg, (1/° C.) | R | $\alpha_g$, (1/° C.) | $\alpha_1$, (1/° C.) |
| True | 14.5 | 0.158 | 0.668 | 28684 | −28.2 | 6.21 | 1.16E−04 | 1.96E−04 |
| Predicted | 18.5 | 0.167 | 0.697 | 27275 | — | — | — | — |

Thermal strain is obtained from one more steps of simple algebra:

$$\varepsilon_{th}(T) = \varepsilon_{th}(T)_{10kg} = \ldots = \varepsilon_{th}(T)_{1g} = \varepsilon_{total}(T)_{10kg} - \sigma_{9kg}/S(T)(10/9) =$$
$$\varepsilon_{total}(T)_{10kg} - [\varepsilon_{total}(T)_{10kg} - \varepsilon_{total}(T)_{1k}](10/9)$$

Repeating the process for a different temperature range provides one continuous CTE versus temperature. Because this simulation does not include error terms, the same parameters for CTE would be obtained.

Figure 7:
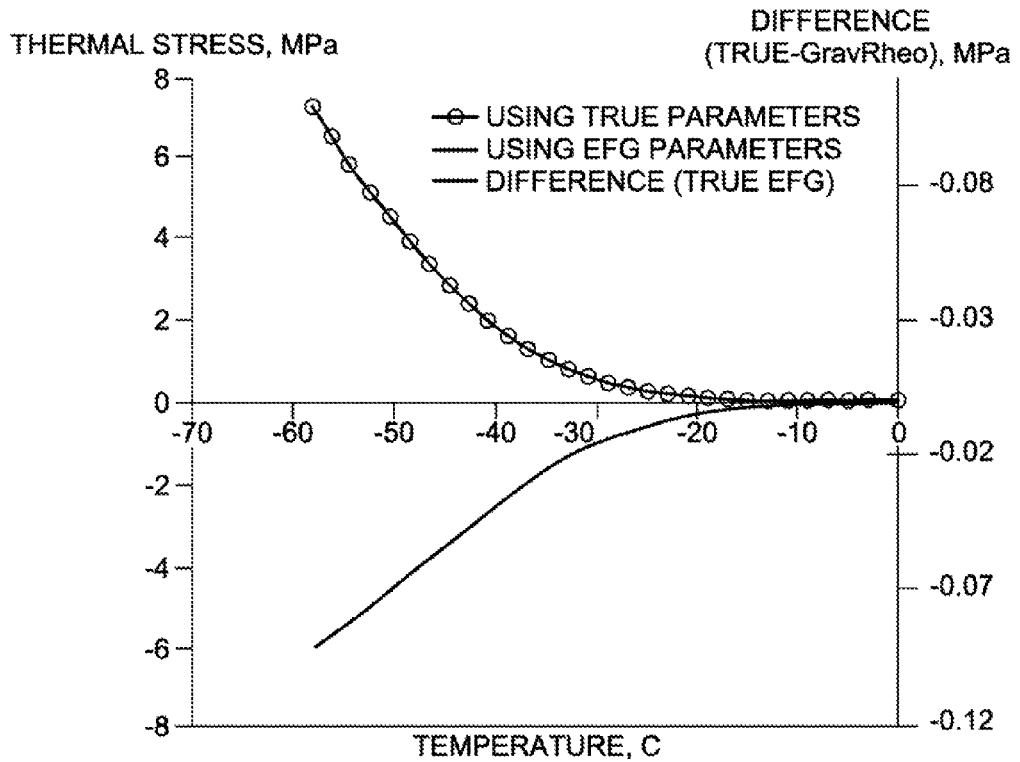
FIG. 7 illustrates thermal stress development calculated using true values and derived parameters in accordance with one embodiment of the present invention.

One of the utility of rheological and thermal characterization is to evaluate thermal stress development within asphalt when contraction is prevented. Thermal stress of the asphalt tested were calculated with both sets of parameters (true and predicted) and they agree as well as illustrated in FIG. 7.

While the present invention has been illustrated by the description of embodiments thereof, and while the embodiments have been described in considerable detail, it is not the intention of the applicants to restrict or in any way limit the scope of the appended claims to such detail. Additional advantages and modifications will readily appear to those skilled in the art. Therefore, the invention, in its broader aspects, is not limited to the specific details, the representative apparatus, and illustrative examples shown and described. Accordingly, departures may be made from such details without departing from the spirit or scope of the applicant's general inventive concept.

I claim:

1. A method for determining properties of an asphalt material, the method comprising:
   measuring respective current deformations of a plurality of samples of the asphalt material;
   repeating the measuring step over a plurality of temperatures that change at a predetermined rate;
   calculating a plurality of measured total strain values as a function of the deformations and the temperatures;
   calculating respective creep strains, at different ones of the plurality of temperatures, based on the total strains as a function of applied stresses;
   calculating respective creep stiffnesses as a function of the temperatures;
   determining a combined creep curve based on the respective creep stiffnesses;
   deriving a theoretical creep curve; and
   fitting the theoretical creep curve with the combined creep curve to determine a master creep curve function and a time-temperature shift function.

2. The method for determining properties of an asphalt material as set forth in claim 1, wherein the step of measuring is repeated every 10 seconds over the plurality of temperatures.

3. The method for determining properties of an asphalt material as set forth in claim 2, further including:
   raising the temperature at a rate of about 10° C. every hour.

4. The method for determining properties of an asphalt material as set forth in claim 1, wherein:
   the step of fitting includes calculating a total difference as a sum of squares of the differences.

5. The method for determining properties of an asphalt material as set forth claim 1, further including:
   determining a thermal expansion coefficient as a function of temperature based on the measured total strain values and calculated creep stiffness.

6. The method for determining properties of an asphalt material as set forth in claim 1, wherein the master creep curve and time-temperature shift function are determined simultaneously;
   the step of determining the master creep stiffness, the temperature shift factor, and the thermal expansion coefficient of the asphalt material simultaneously determines the master creep stiffness, the temperature shift factor, and the thermal expansion coefficient.

7. The method for determining properties of an asphalt material as set forth in claim 1, wherein the measuring includes:
   measuring the dimensions of the samples via linear variable displacement transducers.

8. The method for determining properties of an asphalt material as set forth in claim 7, wherein the measuring includes:
   measuring the dimensions of the samples via capacitive sensors.

9. A system for determining properties of an asphalt material, the system comprising:
   a chamber, a temperature in the chamber being varied as a function of time;
   a plurality of samples of the asphalt material in the chamber;
   a plurality of respective measuring devices for measuring deformations of the asphalt material as the temperature in the chamber changes at a predetermined rate;
   a memory device for storing a plurality of the dimensions;
   a computing device for calculating a plurality of measured total strain values as a function of the deformations and temperatures, calculating respective creep strains, at different ones of the plurality of temperatures, based on the total strain values as a function of applied stresses, calculating respective creep stiffnesses as a function of the temperatures, determining a combined creep curve based on the respective creep stiffnesses, deriving a theoretical creep curve, and fitting the theoretical creep curve with the combined creep curve to determine a master creep curve function and a time-temperature shift function.

10. The system for determining properties of an asphalt material as set forth in claim 9, wherein the measuring devices include:
   linear variable displacement transducers.

11. The system for determining properties of an asphalt material as set forth in claim 10, wherein:
   the measuring devices include capacitive sensors.

12. The system for determining properties of an asphalt material as set forth in claim 9, wherein the computing device controls the temperature to raise in the chamber at a rate of about 10° C. every hour.

13. The system for determining properties of an asphalt material as set forth in claim 9, wherein the computing device determines the expansion of the samples about every 10 seconds.

14. The system for determining properties of an asphalt material as set forth in claim 9, wherein the computing device fits the theoretical creep curve with the combined creep curve to determine the master creep curve function and the time-temperature shift function by calculating a total difference as a sum of squares of the differences.

15. The system for determining properties of an asphalt material as set forth in claim 9, wherein the thermal expansion coefficient of the asphalt material is determined as a function of temperature based on the measured total strain values and calculated creep stiffness.

* * * * *